US009007436B2

(12) United States Patent
Kawata et al.

(10) Patent No.: US 9,007,436 B2
(45) Date of Patent: Apr. 14, 2015

(54) IMAGE DATA RECEIVING APPARATUS AND IMAGE DATA TRANSMISSION SYSTEM

(71) Applicant: Olympus Medical Systems Corp., Tokyo (JP)

(72) Inventors: Susumu Kawata, Hachioji (JP); Takahiro Tanabe, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/048,504

(22) Filed: Oct. 8, 2013

(65) Prior Publication Data

US 2014/0092216 A1    Apr. 3, 2014

Related U.S. Application Data

(63) Continuation of application No. PCT/JP2013/063803, filed on May 17, 2013.

(30) Foreign Application Priority Data

May 24, 2012    (JP) .................................. 2012-118777

(51) Int. Cl.
*H04N 5/378* (2011.01)
*A61B 1/00* (2006.01)
*G02B 23/24* (2006.01)

(52) U.S. Cl.
CPC ............ *H04N 5/378* (2013.01); *G02B 23/2476* (2013.01); *A61B 1/00009* (2013.01)

(58) Field of Classification Search
CPC ....... A61B 1/04; G02B 23/2476; H04N 5/378
See application file for complete search history.

(56) References Cited

U.S. PATENT DOCUMENTS

| 6,044,421 | A  |   | 3/2000 | Ishii |           |
|-----------|----|---|--------|-------|-----------|
| 2007/0177010 | A1 |   | 8/2007 | Murata |           |
| 2013/0194445 | A1 | * | 8/2013 | Brown et al. | 348/222.1 |

FOREIGN PATENT DOCUMENTS

| JP | 04-197331 A | 7/1992 |
|----|-------------|--------|
| JP | 10-322404 A | 12/1998 |

(Continued)

OTHER PUBLICATIONS

International Search Report dated Jun. 25, 2013 issued in PCT/JP2013/063803.

*Primary Examiner* — Andy Rao
*Assistant Examiner* — Tyler Edwards
(74) *Attorney, Agent, or Firm* — Scully, Scott, Murphy & Presser, PC

(57) ABSTRACT

An image data receiving apparatus includes: a first receiving section that receives a first signal including serial data according to image data; a second receiving section that receives a second signal including serial data that is different from the serial data included in the first signal; a first conversion section that converts the serial data included in the first signal into parallel data and outputs the parallel data; a second conversion section that converts the serial data included in the second signal into parallel data and outputs the parallel data; a bit drift amount detecting section that obtains information indicating a degree of drift of the parallel data outputted from the second conversion section from a predetermined bit pattern; and a bit shifting section that shifts the parallel data outputted from the first conversion section according to the information obtained by the bit drift amount detecting section.

8 Claims, 3 Drawing Sheets

(56) References Cited

FOREIGN PATENT DOCUMENTS

| JP | 2007-201895 A | 8/2007 |
| JP | 2009-233178 A | 10/2009 |
| JP | 4512639 B2 | 7/2010 |
| WO | WO 2007/004428 A1 | 1/2007 |

* cited by examiner

IMAGE DATA RECEIVING APPARATUS AND IMAGE DATA TRANSMISSION SYSTEM

CROSS REFERENCE TO RELATED APPLICATION

This application is a continuation application of PCT/JP2013/063803 filed on May 17, 2013 and claims benefit of Japanese Application No. 2012-118777 filed in Japan on May 24, 2012, the entire contents of which are incorporated herein by this reference.

BACKGROUND OF THE INVENTION

1. Field of the Invention

The present invention relates to an image data receiving apparatus and an image data transmission system, and specifically relates to an image data receiving apparatus and an image data transmission system for transmission of image data obtained as a result of an image of an object being picked up.

2. Description of the Related Art

Endoscope systems including, as a main part thereof, an endoscope that picks up an image of an object in a subject to obtain an image and an endoscope signal processing apparatus that performs various types of signal processing on the image obtained by the endoscope have conventionally been used.

Also for endoscope systems such as described above, for example, a configuration such as disclosed in Japanese Patent Application Laid-Open Publication No. 2009-233178 in which A/D conversion processing for an analog image obtained as a result of an image of an object being picked up is performed inside the endoscope and digital data (image data) obtained as a result of the A/D conversion processing is transmitted to the endoscope signal processing apparatus is increasingly employed in recent years.

More specifically, Japanese Patent Application Laid-Open Publication No. 2009-233178 discloses a configuration in which A/D conversion processing for an analog picked-up image signal obtained as a result of an image of an object being picked up is performed inside an endoscope and a digital signal obtained as a result of the A/D conversion processing is transmitted to an endoscope signal processing apparatus as a digital transmission signal.

SUMMARY OF THE INVENTION

An image data receiving apparatus according to an aspect of the present invention includes: a first receiving section that receives a first signal from an image pickup apparatus, the first signal including serial data generated according to image data obtained as a result of an image of an object being picked up by the image pickup apparatus; a second receiving section that receives a second signal from the image pickup apparatus, the second signal including other serial data that is different from the serial data included in the first signal; a first serial/parallel conversion section that converts the serial data included in the first signal received by the first receiving section into parallel data and outputs the parallel data; a second serial/parallel conversion section that converts the serial data included in the second signal received by the second receiving section into parallel data and outputs the parallel data; a bit drift amount detecting section that obtains information indicating a degree of drift of each bit value included in the parallel data outputted from the second serial/parallel conversion section from each corresponding bit value in a predetermined bit pattern, based on the parallel data outputted from the second serial/parallel conversion section and the predetermined bit pattern; and a bit shifting section that performs bit shifting of the parallel data outputted from the first serial/parallel conversion section according to the information obtained from the bit drift amount detecting section.

An image data transmission system according to an aspect of the present invention includes: an image data sending apparatus including an image pickup section that picks up an image of an object to obtain image data, a first sending section that sends a first signal including serial data generated according to the image data, and a second sending section that sends a second signal including other serial data that is different from the serial data included in the first signal; and an image data receiving apparatus including a first receiving section that receives the first signal sent from the first sending section, a second receiving section that receives the second signal sent from the second sending section, a first serial/parallel conversion section that converts the serial data included in the first signal received by the first receiving section into parallel data and outputs the parallel data, a second serial/parallel conversion section that converts the serial data included in the second signal received by the second receiving section into parallel data and outputs the parallel data, a bit drift amount detecting section that obtains information indicating a degree of drift of each bit value included in the parallel data outputted from the second serial/parallel conversion section from each corresponding bit value in a predetermined bit pattern, based on the parallel data outputted from the second serial/parallel conversion section and the predetermined bit pattern, and a bit shifting section that performs bit shifting of the parallel data outputted from the first serial/parallel conversion section according to the information obtained by the bit drift amount detecting section.

DETAILED DESCRIPTION OF THE PREFERRED EMBODIMENTS

An embodiment of the present invention will be described with reference to the drawings.

Figure 1:
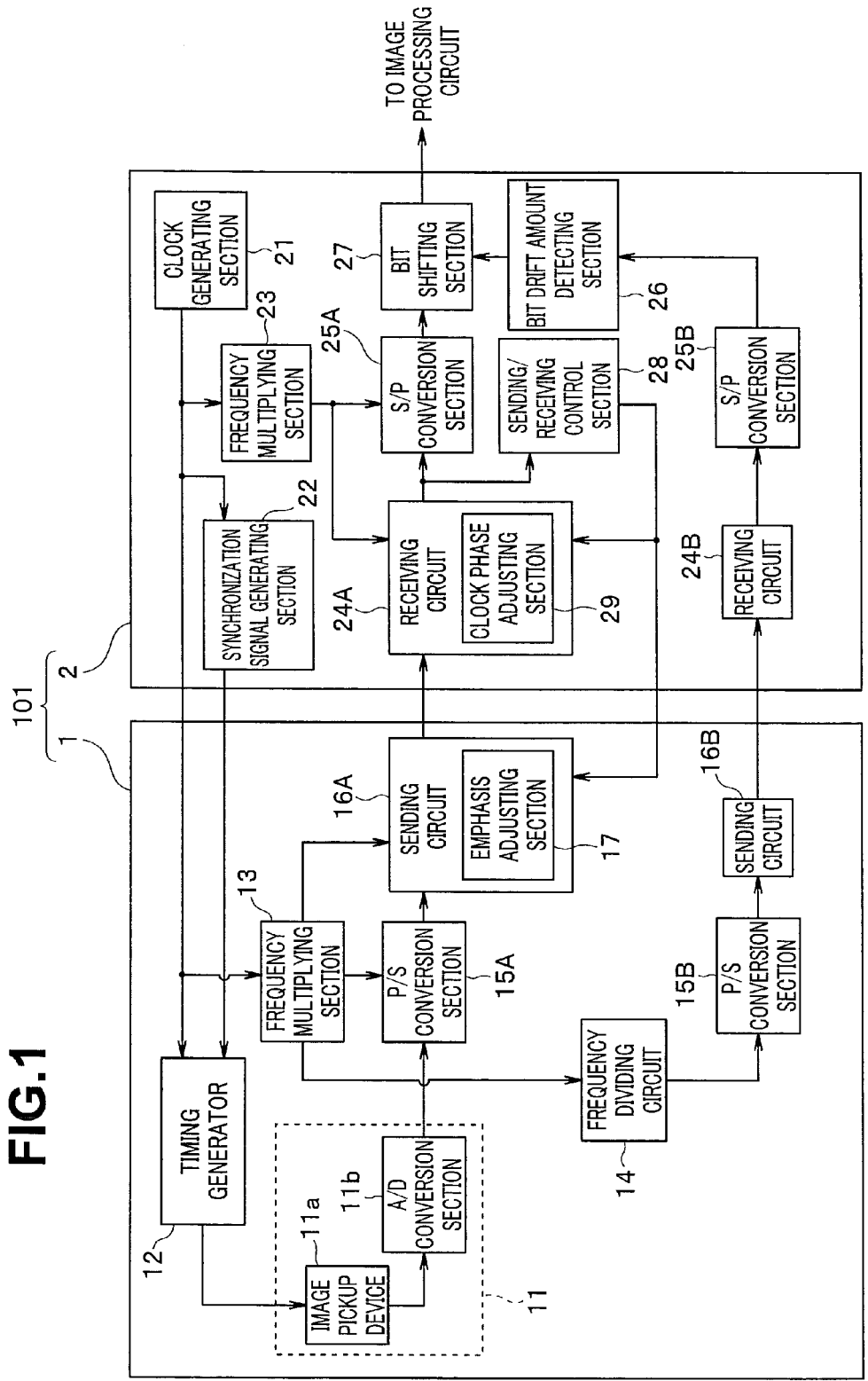
FIG. 1 is a block diagram illustrating a configuration of a main part of an image data transmission system including an image data receiving apparatus according to an embodiment of the present invention.
Figure 2:
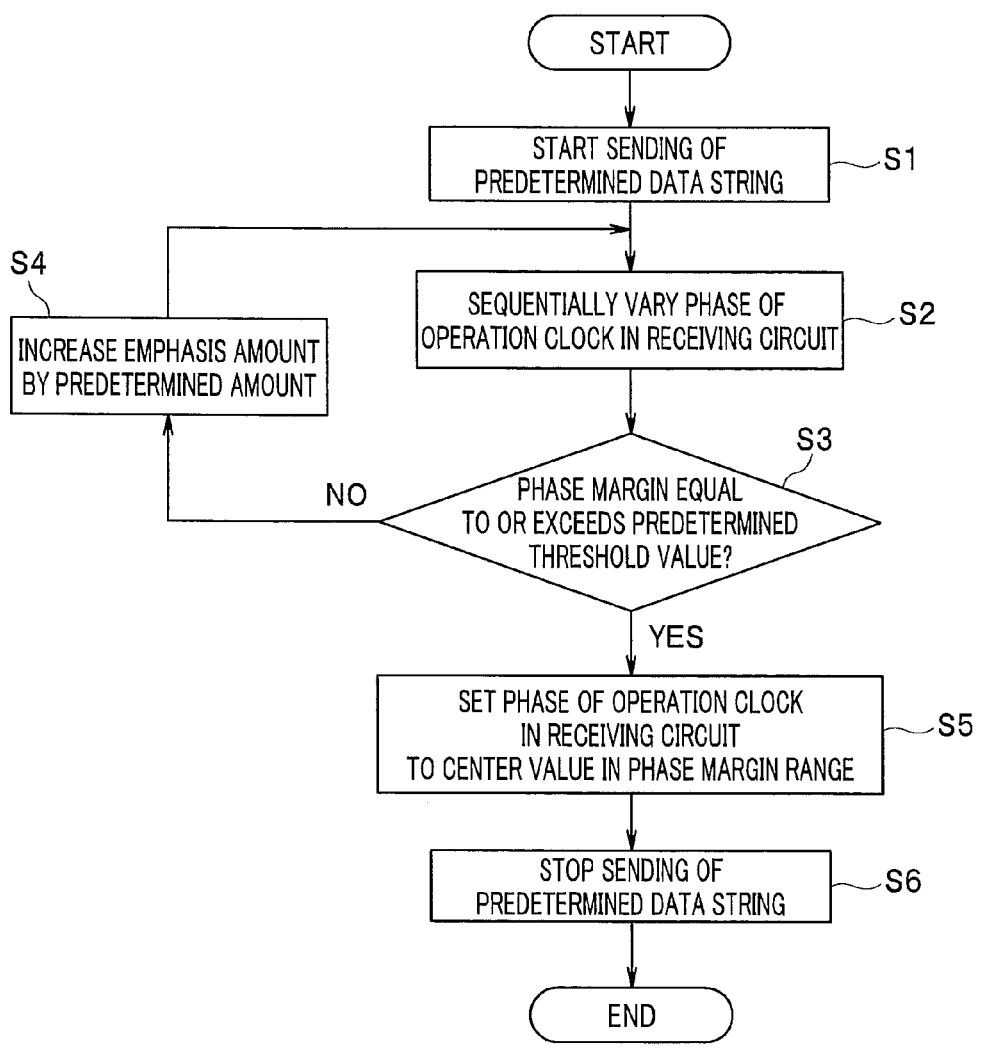
FIG. 2 is a flowchart for describing an example of control performed by a sending/receiving control section according to the present embodiment.

FIGS. 1 and 2 relate to an embodiment of the present invention. FIG. 1 is a block diagram illustrating a configuration of a main part of an image data transmission system according to an embodiment of the present invention.

As illustrated in FIG. 1, an image pickup system 101 is configured as an image data transmission system including an image pickup apparatus 1 including, e.g., a camera head of a videoscope or a rigid endoscope, and a camera control unit (hereinafter referred to as "CCU") 2 that sends/receives various types of signals and data to/from the image pickup apparatus 1.

The image pickup apparatus 1 having a function as an image data sending apparatus includes an image pickup section 11, a timing generator 12, a frequency multiplying section 13, a frequency dividing circuit 14, P/S (parallel/serial) conversion sections 15A and 15B, sending circuits 16A and 16B, and an emphasis adjusting section 17.

The image pickup section 11 includes an image pickup device 11a that includes, e.g., a CCD, and an A/D (analog/digital) conversion section 11b.

The image pickup device 11a is configured so that the image pickup device 11a is driven in response to an HD (horizontal drive) signal and a VD (vertical drive) signal outputted from the timing generator 12, photoelectrically converts (picks up) an image of an object formed on a light receiving surface via a non-illustrated optical system and outputs an analog picked-up image signal (obtain an image).

The A/D conversion section 11b is configured so as to sample the picked-up image signal outputted from the image pickup device 11a every predetermined period of time to convert a signal level of each pixel in the picked-up image signal into digital data including a predetermined number of bits each having a bit value of 0 or 1 and output the digital data.

In other words, the image pickup section 11 is configured so that the image pickup section 11 can pick up an image of an object to obtain an image and obtain digital data (image data) of the image.

The timing generator 12 generates an HD signal and a VD signal for determining a timing for driving the image pickup device 11a, based on a clock signal and a synchronization signal outputted from the CCU 2, and outputs the HD signal and the VD signal.

The frequency multiplying section 13 has an error detection function that can detect an error in the clock signal outputted from the CCU 2. The frequency multiplying section 13 is configured so as to reset the clock signal based on a result of error detection by the error detection function, multiply a frequency of the reset clock signal by a predetermined magnification, and output the multiplied clock signal to each of the frequency dividing circuit 14, the P/S conversion section 15A and the sending circuit 16A.

The frequency dividing circuit 14 is configured so as to divide the frequency of the clock signal outputted from the frequency multiplying section 13 according to the number of bits for one pixel in the digital data outputted from the image pickup section 11 to generate a frequency-divided clock signal and output the frequency-divided clock signal to the P/S conversion section 15B.

More specifically, the frequency dividing circuit 14 is configured so as to, for example, where N-bit data is outputted from the image pickup section 11 as data for one pixel, output a frequency-divided clock signal generated as a result of the frequency of the clock signal outputted from the frequency multiplying section 13 being divided by N to the P/S conversion section 15B.

The P/S conversion section 15A includes, e.g., a serializer and is configured so as to convert respective bit values in the digital data outputted (in parallel) from the image pickup section 11 into serial data based on an operation clock according to the frequency of the clock signal outputted from the frequency multiplying section 13 and output the serial data to the sending circuit 16A.

The P/S conversion section 15B includes, e.g., a serializer, and is configured so as to convert the frequency-divided clock signal outputted from the frequency dividing circuit 14 into serial data and output the serial data to the sending circuit 16B.

The sending circuit 16A includes, e.g., a buffer and a driver, and is configured so as to convert the digital data outputted (serially) from the P/S conversion section 15A into a differential transmission signal of a predetermined format such as an LVDS format.

Also, the sending circuit 16A includes an emphasis adjusting section 17 that can adjust an amount of emphasis for a differential transmission signal to be sent to a receiving circuit 24A (which will be described later) in the CCU 2, based on a control signal outputted from a sending/receiving control section 28 (which will be described later) in the CCU 2.

According to the above-described configuration of the sending circuit 16A, it is possible that: digital data outputted (serially) from the P/S conversion section 15A is converted into a differential transmission signal of a predetermined format; the differential transmission signal resulting from the conversion is subjected to a modulation to add an amount of emphasis set in advance by control performed by the sending/receiving control section 28 (which will be described later) to the differential transmission signal; and furthermore, the differential transmission signal subjected to the modulation is sent to the CCU 2 at a transmission rate according to the frequency of the clock signal outputted from the frequency multiplying section 13.

The sending circuit 16B includes, e.g., a buffer and a driver, and is configured so as to convert the frequency-divided clock signal (that has been converted into serial data) outputted from the P/S conversion section 15B into a differential transmission signal of a predetermined format such as the LVDS format and send the differential transmission signal to the CCU 2.

According to the above-described configurations of the frequency dividing circuit 14, the sending circuit 16A and the sending circuit 16B, a transmission rate of the differential transmission signal outputted from the sending circuit 16B is set to be a 1/N of a transmission rate of the differential transmission signal outputted from the sending circuit 16A.

On the other hand, the CCU 2 having a function as an image data receiving apparatus includes a clock generating section 21, a synchronization signal generating section 22, a frequency multiplying section 23, receiving circuits 24A and 24B, S/P (serial/parallel) conversion sections 25A and 25B, a bit drift amount detecting section 26, a bit shifting section 27, the sending/receiving control section 28 and a clock phase adjusting section 29.

The clock generating section 21 generates a clock signal having a predetermined frequency, which is used for operation of respective components of the image pickup apparatus 1 and the CCU 2, and outputs the clock signal to the image pickup apparatus 1 and the synchronization signal generating section 22.

The synchronization signal generating section 22 generates a synchronization signal used for generation of an HD signal and a VD signal, based on the clock signal outputted from the clock generating section 21, and outputs the synchronization signal to the image pickup apparatus 1.

The frequency multiplying section 23 is configured so as to multiply a frequency of the clock signal outputted from the clock generating section 21 by a predetermined magnification (equal to the magnification in the frequency multiplying section 13) and output the multiplied clock signal to the receiving circuit 24A and the S/P conversion section 25A.

The receiving circuit 24A includes, e.g., a pulse transformer, and is configured so as to receive the differential transmission signal sent from the sending circuit 16A in the image pickup apparatus 1, based on an operation clock according to the frequency of the clock signal outputted from the frequency multiplying section 23.

Also, the receiving circuit 24A is configured so as to convert the differential transmission signal that has been modulated as described above into (serial) digital data and output the digital data resulting from the conversion to the S/P conversion section 25A and the sending/receiving control section 28.

Furthermore, the receiving circuit 24A includes a clock phase adjusting section 29 that can adjust a phase of an operation clock that determines a timing for receiving the differential transmission signal sent from the sending circuit 16A, based on a control signal outputted from the sending/receiving control section 28.

According to the above-described configuration of the receiving circuit 24A, it is possible that a differential transmission signal sent from the sending circuit 16A in the image pickup apparatus 1 is received based on an operation clock according to a frequency of a clock signal outputted from the frequency multiplying section 23 at a timing corresponding to a phase of the clock signal, the phase being set in advance by the control performed by the sending/receiving control section 28.

The receiving circuit 24B includes, e.g., a pulse transformer, and is configured so as to receive the differential transmission signal sent from the sending circuit 16B in the image pickup apparatus 1, and restore a frequency-divided clock signal according to the received differential transmission signal as serial data and output the frequency-divided clock signal to the S/P conversion section 25B.

The S/P conversion section 25A includes, e.g., a deserializer, and is configured so as to convert respective bit values in the digital data outputted (serially) from the receiving circuit 24A into parallel data at an operation rate according to the frequency of the clock signal outputted from the frequency multiplying section 23 and output the parallel data to the bit shifting section 27.

The S/P conversion section 25B includes, e.g., a deserializer, and is configured to as to convert the frequency-divided clock signal (that has been converted into serial data) outputted from the receiving circuit 24B into parallel data and output the parallel data to the bit drift amount detecting section 26.

The bit drift amount detecting section 26 holds a predetermined bit pattern including a number of bits, the number being equal to that of the frequency-divided clock signal (that has been converted into parallel data) outputted from the S/P conversion section 25B. Then, the bit drift amount detecting section 26 compares the aforementioned predetermined bit pattern and the frequency-divided clock signal outputted from the S/P conversion section 25B to detect a bit drift amount indicating a degree of drift of the respective bit values included in the frequency-divided clock signal (that has been converted into parallel data) outputted from the S/P conversion section 25B from the respective bit values included in the predetermined bit pattern and output information on the detected bit drift amount to the bit shifting section 27.

The bit shifting section 27 is configured so that the bit shifting section 27 can perform correction processing for shifting the respective bit values included in the parallel data outputted from the S/P conversion section 25A according to the bit drift amount information outputted from the bit drift amount detecting section 26, and output the parallel data subjected to the correction processing to an image processing circuit (not illustrated) positioned downstream of the CCU 2.

Also, the bit shifting section 27 is configured so as not to, based on the bit drift amount information outputted from the bit drift amount detecting section 26, if it is detected that the bit drift amount is zero, perform correction processing on the parallel data outputted from the S/P conversion section 25A but output the parallel data outputted from the S/P conversion section 25A directly to the image processing circuit (not illustrated).

The sending/receiving control section 28 is configured to generate a control signal for controlling the sending circuit 16A and the receiving circuit 24A based on the digital data (serially) outputted from the receiving circuit 24A and output the control signal. Note that details of the control performed by the sending/receiving control section 28 for the sending circuit 16A and the receiving circuit 24A will be described later.

Next, operation, etc., of the image pickup system 101 according to the present embodiment will be described below. Note that hereinafter, except where specifically noted, the description will be provided taking a case where eight-bit data is generated as data for one pixel as an example. FIG. 2 is a flowchart for describing an example of control performed by a sending/receiving control section according to the present embodiment.

First, substantially immediately after application of power to the respective components in the image pickup system 101, a clock signal generated by the clock generating section 21 is sent to the frequency multiplying sections 13 and 23, the clock signal multiplied by the frequency multiplying section 13 is outputted to the sending circuit 16A, and the clock signal multiplied by the frequency multiplying section 23 is outputted to the receiving circuit 24A.

Subsequently, the sending/receiving control section 28 sends a control signal for starting sending of a predetermined data string including predetermined bit values to the sending circuit 16A (step S1 in FIG. 2), and also sends a control signal for sequentially varying a phase of an operation clock that determines a timing for receiving a differential transmission signal sent from the sending circuit 16A (by means of operation of the clock phase adjusting section 29) to the receiving circuit 24A (step S2 in FIG. 2).

The sending/receiving control section 28 compares digital data sequentially outputted from the receiving circuit 24A along with the variation of the operation clock phase by the clock phase adjusting section 29, and the predetermined data string sent by means of control of the sending circuit 16A to measure a phase margin as a phase range in which the predetermined data string can normally be received by the receiving circuit 24A, and determines whether or not the measured phase margin is equal to or exceeds a predetermined threshold value (step S3 in FIG. 2).

Then, if a result of the determination in step S3 in FIG. 2 is that the phase margin is smaller than the predetermined threshold value, the sending/receiving control section 28 sends a control signal for increasing an amount of emphasis to be added to the differential transmission signal (by means of operation of the emphasis adjusting section 17) by a predetermined amount to the sending circuit 16A (step S4 in FIG. 2) and then returns to step S2 in FIG. 2 and performs the processing, etc.

Also, if a result of the determination in step S3 in FIG. 2 is that the phase margin is equal to or exceeds the predetermined threshold value, the sending/receiving control section 28 sends a control signal for setting the phase of the operation clock (timing for receiving the differential transmission signal sent from the sending circuit 16A) so that the phase becomes a center value in a range of phase margin measured immediately before obtainment of the determination result, to the receiving circuit 24A (step S5 in FIG. 2), and sends a control signal for adding the emphasis amount immediately before obtainment of the determination result, to the differential transmission signal to the sending circuit 16A and then sends a control signal for stopping the sending of the predetermined data string, to the sending circuit 16A (step S6 in FIG. 2).

Then, as a result of a series of control indicated in FIG. 2 being performed, a signal level of the differential transmission signal outputted from the sending circuit 16A can be set to a proper signal level according to a transmission distance from the image pickup apparatus 1 to the CCU 2, and as a result, power consumption for differential transmission signal transmission can be optimized for each of various combinations of an image pickup apparatus 1 and a CCU 2.

On the other hand, after the series of control indicated in FIG. 2 being performed, a clock signal generated by the clock generating section 21 and a synchronization signal generated by the synchronization signal generating section 22 are outputted to the timing generator 12.

The timing generator 12 generates an HD signal and a VD signal for determining a timing for driving the image pickup device 11a, based on the clock signal and the synchronization signal outputted from the CCU 2, and outputs the HD signal and the VD signal.

The image pickup device 11a is driven in response to the HD signal and the VD signal supplied from the timing generator 12 to pick up an image of an object and outputs an analog picked-up image signal.

The A/D conversion section 11b samples the picked-up image signal outputted from the image pickup device 11a every predetermined period of time to convert a signal level of each pixel in the picked-up image signal into eight-bit digital data and output the eight-bit digital data.

The frequency dividing circuit 14 outputs a frequency-divided clock signal generated by dividing a frequency of the clock signal outputted from the frequency multiplying section 13 by eight, to the P/S conversion section 15B.

The P/S conversion section 15A serializes respective bit values in the eight-bit digital data outputted (in parallel) from the image pickup section 11, based on an operation clock according to the frequency of the clock signal outputted from the frequency multiplying section 13, and outputs the serialized bit values to the sending circuit 16A.

The P/S conversion section 15B converts the frequency-divided clock signal outputted from the frequency dividing circuit 14 into serial data and outputs the serial data to the sending circuit 16B.

The sending circuit 16A converts the digital data (serially) outputted from the P/S conversion section 15A into a differential transmission signal of a predetermined format, and performs a modulation to add the amount of emphasis set through the series of control indicated in FIG. 2 to the differential transmission signal resulting from the conversion, and sends the differential transmission signal subjected to the modulation to the receiving circuit 24A at a transmission rate according to the frequency of the clock signal outputted from the frequency multiplying section 13.

The sending circuit 16B converts the frequency-divided clock signal (that has been converted into serial data) outputted from the P/S conversion section 15B into a differential transmission signal of a predetermined format such as the LVDS format and sends the differential transmission signal to the receiving circuit 24B.

The receiving circuit 24A receives the differential transmission signal sent from the sending circuit 16A in the image pickup apparatus 1 at a receiving timing corresponding to an operation clock according to the frequency of the clock signal outputted from the frequency multiplying section 23, the receiving timing being set through the series of control indicated in FIG. 2, converts the received differential transmission signal into (serial) digital data, and outputs the digital data resulting from the conversion to the S/P conversion section 25A.

The receiving circuit 24B receives the differential transmission signal sent from the sending circuit 16B in the image pickup apparatus 1, and restores a frequency-divided clock signal according to the received differential transmission signal as serial data and outputs the serial data to the S/P conversion section 25B.

The S/P conversion section 25A converts the respective bit values in the digital data outputted (serially) from the receiving circuit 24A into parallel data at an operation speed according to the frequency of the clock signal outputted from the frequency multiplying section 23 and outputs the parallel data to the bit shifting section 27.

The S/P conversion section 25B converts the frequency-divided clock signal (that has been converted into serial data) outputted from the receiving circuit 24A into parallel data and outputs the parallel data to the bit drift amount detecting section 26.

The bit drift amount detecting section 26 compares the eight-bit predetermined bit pattern, and the frequency-divided clock signal outputted by eight bits by the S/P conversion section 25B to detect a bit drift amount indicating a degree of drift of the respective bit values included in the frequency-divided clock signal outputted from the S/P conversion section 25B from the respective bit values included in the predetermined bit pattern, and outputs information on the detected bit drift amount to the bit shifting section 27.

The bit shifting section 27 performs correction processing for shifting the respective bit values included in the parallel data outputted by eight bits from the S/P conversion section 25A, according to the bit drift amount information outputted from the bit drift amount detecting section 26, and outputs the parallel data subjected to the correction processing to the image processing circuit (not illustrated).

More specifically, based on the bit drift amount information outputted from the bit drift amount detecting section 26, for example, if it is detected that a one-bit drift occurs, the bit shifting section 27 performs correction processing for shifting, by one bit, the respective bit values in the eight-bit parallel data inputted at the timing when the occurrence of the drift was detected, and outputs the parallel data subjected to the correction processing to the image processing circuit (not illustrated).

Then, the processing and operation described above are performed in, e.g., the bit shifting section 27, enabling parallel data subjected to correction processing (parallel data with the bits shifted) for proper synchronization between the image pickup apparatus 1 and the CCU 2 to be outputted to the image processing circuit (not illustrated) positioned downstream of the CCU 2.

As described above, according to the present embodiment, when a differential transmission signal is sent from the sending circuit 16A to the receiving circuit 24A, data such as a synchronization pattern used for synchronization between the image pickup apparatus 1 and the CCU 2 is not superimposed on the differential transmission signal. As a result, the present embodiment enables enhancement of signal quality when a signal including image data is received compared to the conventional techniques.

Also, as described above, the present embodiment enables the image pickup apparatus 1 and the CCU 2 to be properly synchronized without superimposing data such as a synchronization pattern on a differential transmission signal to be sent from the sending circuit 16A to the receiving circuit 24A.

Also, as described above, according to the present embodiment, correction processing (bit shifting) for properly synchronizing the image pickup apparatus 1 and the CCU 2 is performed in the bit shifting section 27 at every timing of bit drift amount information being outputted from the bit drift amount detecting section 26. As a result, according to the present embodiment, even if a sudden bit drift occurs due to, e.g., a disturbance, the bit drift can immediately be corrected, enabling a period in which the image pickup apparatus 1 and the CCU 2 are not properly synchronized to be minimized.

Figure 3:
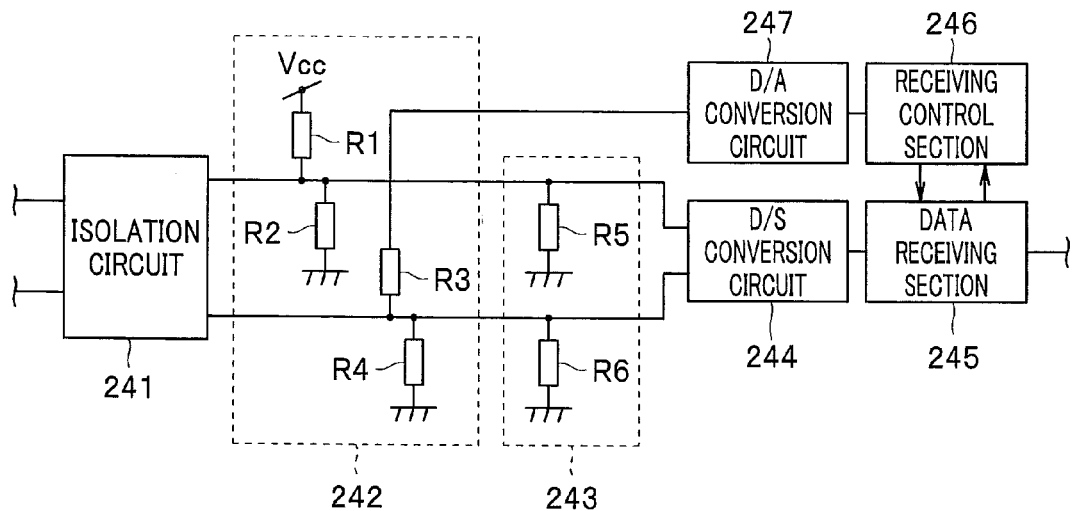
FIG. 3 is a diagram illustrating an example of a configuration that can be incorporated into a receiving circuit according to the present embodiment.

Note that the receiving circuit 24A in the present embodiment may include, for example, the components such as illustrated in FIG. 3 so that the receiving circuit 24A can receive digital data (image data) with duty cycle distortion occurring in a differential transmission signal suppressed while a transition time period restriction on the differential transmission signal is eased. FIG. 3 is a diagram illustrating an example of a configuration that can be incorporated into a receiving circuit according to the present embodiment.

More specifically, for example, as illustrated in FIG. 3, the receiving circuit 24A in the present embodiment may include an isolation circuit 241 to which a differential transmission signal sent from the sending circuit 16A is inputted, a biasing circuit 242 connected downstream of the isolation circuit 241, a terminal circuit 243 connected downstream of the biasing circuit 242, a D/S (differential/single-end) conversion circuit 244 that converts the differential transmission signal that has passed through the terminal circuit 243 into a single-end signal, a data receiving section 245 that receives digital data according to the single-end signal outputted from the D/S conversion circuit 244, and a receiving control section 246, and a D/A conversion circuit 247.

The biasing circuit 242 includes a resistance R1 connected so as to apply a bias voltage corresponding to a power supply voltage Vcc to one signal wire (hereinafter also referred to as "first signal wire") of two signal wires for differential transmission signal transmission, a resistance R2 connected between the first signal wire and a ground voltage GND, a resistance R3 connected so as to apply a bias voltage according to an output voltage of the D/A conversion circuit 247 to the other signal wire (hereinafter also referred to as "second signal wire") of the two signal wires, and a resistance R4 connected between the second signal wire and the ground voltage GND.

The terminal circuit 243 includes a terminal resistance R5 connected between the first signal wire and the ground voltage GND, and a terminal resistance R6 connected between the second signal wire and the ground voltage GND.

The receiving control section 246 is configured so that the receiving control section 246 can output a control signal for changing the bias voltage applied to the second signal wire by the biasing circuit 242, to the D/A conversion circuit 247. Along with a change in output voltage of the D/A conversion circuit 247 in response to the control signal outputted from the receiving control section 246, the bias voltage applied to the second signal wire via the resistance R3 in the biasing circuit 242 is changed.

Also, the receiving control section 246 is configured so that the receiving control section 246 can measure a phase margin for the data receiving section 245 where an arbitrary bias voltage is applied to the second signal wire in the biasing circuit 242, for example, by performing operation to determine whether or not the data receiving section 245 can normally receive digital data while a phase of an operation clock in the data receiving section 245 is sequentially varied each time the aforementioned control signal is outputted to the D/A conversion circuit 247.

Furthermore, the receiving control section 246 is configured so that the receiving control section 246 can, based on a result of the measurement of the phase margin described above, output a control signal for applying a bias voltage for maximizing the phase margin to the second signal wire in the biasing circuit 242, to the D/A conversion circuit 247.

It is desirable that the operation of the receiving control section 246 for phase margin measurement and bias voltage change be performed, for example, as in the series of processing indicated in FIG. 2, using a predetermined data string sent from the sending circuit 16A substantially immediately after application of power to the respective components of the image pickup system 101.

Accordingly, the receiving circuit 24A includes a configuration such as described above, enabling digital data (image data) to be received with duty cycle distortion, which occurs due to variations in the D/S conversion circuit 244, suppressed while the transition time period restriction on a differential transmission signal is eased.

Figure 4:
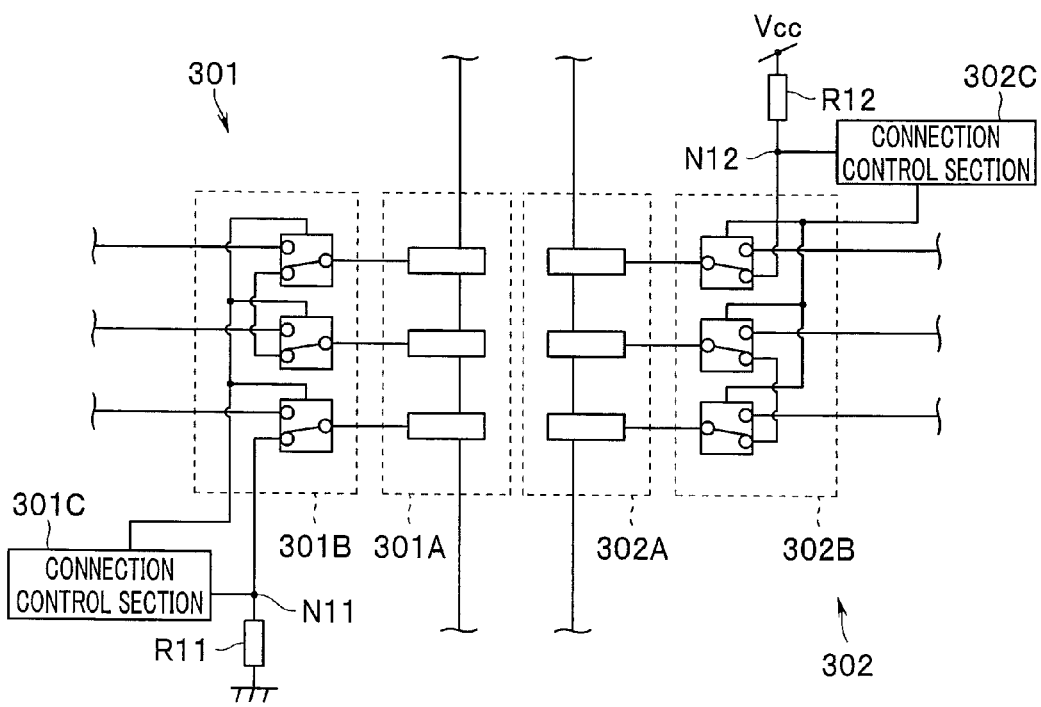
FIG. 4 is a diagram illustrating an example of a configuration of a connection interface that can be employed in the image data transmission system according to the present embodiment.

According to the present embodiment, a connection interface configuration such as illustrated in FIG. 4 may be employed to enable a user to be notified of occurrence of an abnormality in electrical connection between the image pickup apparatus 1 and the CCU 2 before operation for, e.g., pickup of an image of an object. FIG. 4 is a diagram illustrating an example of a connection interface configuration that can be employed in an image data transmission system according to the present embodiment.

More specifically, according to the present embodiment, for example, a connection interface configuration in which an electrical connection section 301 such as illustrated in FIG. 4 is provided around a connector (not illustrated) of an end portion of a cable extending out from the image pickup apparatus 1 and an electrical connection section 302 such as illustrated in FIG. 4 is provided around an entry point (not illustrated) for the connector in the CCU 2 may be employed.

The electrical connection section 301 includes a contact section 301A including a plurality of electrical contacts, a relay switch section 301B including a number of switches, the number being equal to the number of electrical contacts in the contact section 301A, a connection control section 301C that performs control for turning-on/off of the respective switches in the relay switch section 301B, and a resistance R11 connected to a node N11 and the ground voltage GND.

The relay switch section 301B is configured so that the relay switch section 301B can make the respective switches operate to provide either a conductive state in which the respective electrical contacts in the contact section 301A are connected to respective normal connection destinations or a non-conductive state in which the respective electrical contacts in the contact section 301A are connected to respective other connection destinations that are different from the normal connection destinations, based on the control performed by the connection control section 301C.

Also, the relay switch section 301B is configured so as to maintain a non-conductive state if the electrical connection sections 301 and 302 are not connected.

The connection control section 301C includes, e.g., a timer that starts operating according to a voltage applied to the node N11, and is configured to, if it is detected that a predetermined period of time has elapsed from a start of operation of the timer, perform control for changing the state of (the respective switches in) the relay switch section 301B from a non-conductive state to a conductive state.

The electrical connection section 302 includes a contact section 302A including a plurality of electrical contacts, a relay switch section 302B including a number of switches, the number being equal to the number of electrical contacts in the contact section 302A, a connection control section 302C that performs control for turning-on/off of the respective switches in the relay switch section 302B, and a resistance R12 connected between a node N12 and the power supply voltage Vcc.

The relay switch section 302B is configured so that the relay switch section 302B can make the respective switches operate to provide either a conductive state in which the respective electrical contacts in the contact section 302A are connected to respective normal connection destinations or a non-conductive state in which the respective electrical contacts in the contact section 302A are connected to respective other connection destinations that are different from the normal connection destinations, based on the control performed by the connection control section 302C.

Also, the relay switch section 302B is configured so as to maintain a non-conductive state, if the electrical connection sections 301 and 302 are not connected.

The connection control section 302C is configured so as to perform control to, if it is detected that a voltage of the node N12 is larger than a predetermined value TH (<Vcc) as a result of the voltage of the node N12 being monitored, bring the state of (the respective switches in) the relay switch section 302B into a non-conductive state, and if it is detected that the voltage of the node N12 is equal to or smaller than the predetermined value TH, bring the state of (the respective switches in) the relay switch section 302B into a conductive state.

On the other hand, as illustrated in FIG. 4, in the electrical connection sections 301 and 302, wirings are provided so that if the contact sections 301A and 302A are connected with the relay switch sections 301B and 302B remained in a non-conductive state, the respective components existing at respective positions partway from the node N11 to the node N12 (the respective electrical contacts in the contact section 301A, the respective switches in the relay switch section 301B, the respective electrical contacts in the contact section 302A and the respective switches in the relay switch section 302B) are connected in series.

Therefore, when the electrical connection sections 301 and 302 are connected, voltages resulting from division according to a difference in potential between the power supply voltage Vcc in the electrical connection section 302 and the ground voltage GND in the electrical connection section 301, respective resistance values of the resistances R11 and R12, respective resistance values of the respective electrical contacts in the contact section 301A, respective resistance values of the respective switches in the relay switch section 301B, respective resistance values of the respective electrical contacts in the contact section 302A, and respective resistance values of the respective switches in the relay switch section 302B are respectively applied to the node N11 and the node N12.

Here, the voltage applied to the node N11 when the electrical connection sections 301 and 302 are connected decreases (becomes close to the voltage value of the ground potential) as the number of electrical contacts each having a resistance value increased by, e.g., formation of an oxide film from among the respective electrical contacts included in the contact sections 301A and 302A increases.

Therefore, if it is detected, as a result of the voltage of the node N11 being monitored using the above-described timer, that the voltage applied to the node N11 when the electrical connection sections 301 and 302 are connected is smaller than an operating voltage of the timer, the connection control section 301C estimates that the number of electrical contacts each having a resistance value increased by, e.g., formation of an oxide film is equal to or exceeds a predetermined number, and performs control to maintain the state of (the respective switches in) the relay switch section 301B in a non-conductive state.

Also, if it is detected, as a result of the voltage of the node N11 being monitored using the above-described timer, that a predetermined period of time has elapsed after the voltage applied to the node N11 when the electrical connection sections 301 and 302 are connected becomes equal to or exceeds an operating voltage of the timer, the connection control section 301C estimates that the number of electrical contacts each having a resistance values increased by, e.g., formation of an oxide film is smaller than the predetermined number, and performs control to switch the state of (the respective switches in) the relay switch section 301B from a non-conductive state to a conductive state.

On the other hand, the voltage applied to the node N12 when the electrical connection sections 301 and 302 are connected increases (becomes close to the voltage value of the power supply voltage Vcc) as the number of electrical contacts each having a resistance value increased by, e.g., formation of an oxide film from among the respective electrical contacts included in the contact sections 301A and 302A increases.

Therefore, if it is detected, as a result of the voltage of the node N12 being monitored, that the voltage applied to the node N12 when the electrical connection sections 301 and 302 are connected is larger than the predetermined value TH, the connection control section 302C estimates that the number of electrical contacts each having a resistance value increased by, e.g., formation of an oxide film is equal to or exceeds the predetermined number, and performs control to bring the state of (the respective switches in) the relay switch section 302B into a non-conductive state, and generates a signal including information that can provide a notification that an abnormality occurs in electrical connection between the image pickup apparatus 1 and the CCU 2, and outputs the signal to the image processing circuit (not illustrated) (positioned downstream of the CCU 2). Then, the signal including such information is subjected to image processing by the image processing circuit (not illustrated) and the signal resulting from the image processing is outputted to a display apparatus (not illustrated) such as a monitor, enabling a user to be notified of occurrence of the abnormality in the electrical connection between the image pickup apparatus 1 and the CCU 2.

Also, it is detected, as a result of the voltage of the node N12 being monitored, that the voltage applied to the node N12 when the electrical connection sections 301 and 302 are connected is equal to or smaller than the predetermined value TH, the connection control section 302C estimates that the number of electrical contacts each having a resistance value increased by, e.g., formation of an oxide film is smaller than the predetermined number, and performs control to bring the state of (the respective switches in) the relay switch section 302B to a conductive state.

Note that according to the above-described connection interface configuration, for example, it is possible that the voltage value of the power supply voltage Vcc is adjusted according to, e.g., the total number of electrical contacts included in the contact sections 301A and 302A so that the oxide film can be broken when the electrical connection sections 301 and 302 are connected.

According to the above-described connection interface configuration, a user can be notified of occurrence of an abnormality in the electrical connection between the image pickup apparatus 1 and the CCU 2 before operation for, e.g., pickup of an image of an object is performed, enabling suppression of use of the image pickup system 101a number of time exceeding a durable number of times set in advance.

The present invention is not limited to the above-described embodiment, and it should be understood that various modifications and applications are possible without departing from the spirit of the invention.

What is claimed is:

1. An image data receiving apparatus comprising:
a first receiving section that receives a first signal from an image pickup apparatus, the first signal including serial data that is converted from image data obtained as a result of an image of an object being picked up by the image pickup apparatus, based on an operation clock according to a predetermined clock signal;
a second receiving section that receives a second signal from the image pickup apparatus, the second signal including second serial data that is different from the serial data included in the first signal, the second serial data being converted from a second clock signal generated according to the clock signal;
a first serial/parallel conversion section that converts the serial data included in the first signal received by the first receiving section into first parallel data and outputs the first parallel data;
a second serial/parallel conversion section that converts the second serial data included in the second signal received by the second receiving section into second parallel data and outputs the second parallel data;
a bit drift amount detecting section that obtains information indicating a degree of drift of each bit value included in the second parallel data outputted from the second serial/parallel conversion section from each corresponding bit value in a predetermined bit pattern, based on the second parallel data outputted from the second serial/parallel conversion section and the predetermined bit pattern; and
a bit shifting section that performs bit shifting of the first parallel data outputted from the first serial/parallel conversion section according to the information obtained from the bit drift amount detecting section.

2. The image data receiving apparatus according to claim 1, further comprising a control section that, based on the serial data included in the first signal received by the first receiving section, performs control for adjusting an amount of emphasis added to the first signal to be transmitted to the first receiving section and a receiving timing for the first receiving section to receive the first signal, respectively, so that a period in which the first receiving section can normally receive a predetermined data string has a value equal to or exceeding a predetermined threshold value.

3. The image data receiving apparatus according to claim 1, wherein, upon receipt of a differential transmission signal including a predetermined data string from the image pickup apparatus, the first receiving section adjusts a bias voltage applied to the received differential transmission signal so that a period in which the predetermined data string can normally be received becomes maximum.

4. An image data transmission system comprising:
an image data sending apparatus including
an image pickup section that picks up an image of an object to obtain image data,
a first sending section that sends a first signal including serial data that is converted from the image data based on an operation clock according to a predetermined clock signal, and
a second sending section that sends a second signal including second serial data that is different from the serial data included in the first signal, the second serial data being converted from a second clock signal generated according to the clock signal; and
an image data receiving apparatus including
a first receiving section that receives the first signal sent from the first sending section,
a second receiving section that receives the second signal sent from the second sending section,
a first serial/parallel conversion section that converts the serial data included in the first signal received by the first receiving section into first parallel data and outputs the first parallel data,
a second serial/parallel conversion section that converts the second serial data included in the second signal received by the second receiving section into second parallel data and outputs the second parallel data,
a bit drift amount detecting section that obtains information indicating a degree of drift of each bit value included in the second parallel data outputted from the second serial/parallel conversion section from each corresponding bit value in a predetermined bit pattern, based on the second parallel data outputted from the second serial/parallel conversion section and the predetermined bit pattern, and
a bit shifting section that performs bit shifting of the first parallel data outputted from the first serial/parallel conversion section according to the information obtained by the bit drift amount detecting section.

5. The image data transmission system according to claim 4, wherein the image data receiving apparatus further includes a control section that, based on the serial data included in the first signal received by the first receiving section, performs control for adjusting an amount of emphasis added to the first signal sent from the first sending section and a receiving timing for the first receiving section to receive the first signal, respectively, so that a period in which the first receiving section can normally receive a predetermined data string has a value equal to or exceeding a predetermined threshold value.

6. The image data transmission system according to claim 4, wherein upon receipt of a differential transmission signal including a predetermined data string from the image data sending apparatus, the first receiving section adjusts a bias voltage applied to the received differential transmission signal so that a period in which the predetermined data string can normally be received becomes maximum.

7. The image data transmission system according to claim 4, wherein if data for one pixel included in the image data has N bits, the image data sending apparatus sets a transmission rate of the second signal sent from the second sending section to be 1/N of a transmission rate of the first signal sent from the first sending section.

8. The image data transmission system according to claim 4, wherein when respective electrical connection sections provided in the image data sending apparatus and the image data receiving apparatus are connected, whether or not an abnormality exists in any of the electrical connection sections is detected and if an abnormality in any of the electrical connection sections is detected, a notification of occurrence of the abnormality in electrical connection between the image data sending apparatus and the image data receiving apparatus is provided.

* * * * *